United States Patent [19]

Graham

[11] Patent Number: 4,752,611

[45] Date of Patent: Jun. 21, 1988

[54] ANTICOCCIDIAL 1,2,3-TRAZOLE COMPOUNDS

[75] Inventor: Donald W. Graham, Mountainside, N.J.

[73] Assignee: Merck & Co., Inc., Rahway, N.J.

[21] Appl. No.: 803,037

[22] Filed: Nov. 29, 1985

[51] Int. Cl.⁴ .................... A01N 43/36; C07D 249/06
[52] U.S. Cl. ..................................... 514/359; 548/255
[58] Field of Search .......................... 514/359; 548/255

[56] References Cited

U.S. PATENT DOCUMENTS 4,590,201  5/1986  Bochis et al. .................. 548/255

FOREIGN PATENT DOCUMENTS 151528  8/1985  European Pat. Off. ............ 514/359

OTHER PUBLICATIONS

Harris et al.; C.A. 104:34088r; EPO 151528 5(Amino or Subst. Amino)-1,2,3-Trazoles.
Albert et al., *J. Chem. Soc. Perkins Trans 1,* pp. 427-428 (1978).
Albert, *J. Chem. Soc. Perkins 1,* pp. 461-467 (1972).

*Primary Examiner*—Glennon H. Hollrah
*Assistant Examiner*—D. L. Dinner
*Attorney, Agent, or Firm*—David L. Rose; Michael C. Sudol

[57] ABSTRACT

There are disclosed certain 1,2,3-triazole compounds with a substituted benzyl group at the 1-position, an amido group at the 4-position and a aminomethylene amino group at the 5-position. The compounds are prepared from the corresponding compound wherein the 5-position substituent is amino by treatment with a formimido acetal. The compounds are active anticoccidial agents.

17 Claims, No Drawings

ANTICOCCIDIAL 1,2,3-TRAZOLE COMPOUNDS

BACKGROUND OF THE INVENTION

This invention relates to new chemical compounds and the method of the preparation of the same. It relates further to the use of such new compounds for treating and preventing coccidiosis. This invention still more particularly relates to novel 5-((amino)methylene amino) 1,2,3-triazole compounds and substituted derivatives thereof and the use of the same in the control and treatment of coccidiosis.

Coccidiosis is a wide-spread poultry disease which is produced by infections of protozoa of the genus Eimeria which causes severe pathology in the intestines and ceca of poultry. Some of the most significant of these species are *E. tenella, E. acervulina, E. necatrix, E. brunetti, E. maxima, E. mitis, E. mivati, E. hagani* and *E. praecox*. This disease is generally spread by the birds picking up the infectious organism in droppings on contaminated litter or ground or by way of food or drinking water. The disease is manifested by hemorrhage, accumulation of blood in the ceca, passage of blood to the droppings, weakness and digestive disturbances. The disease often terminates in the death of the animal but the fowl which survive severe infections have had their market value substantially reduced as a result of the infection. Coccidiosis is therefore a disease of great economic importance and extensive work has been done to find new and improved methods for controlling and treating coccidial infections in poultry.

SUMMARY OF THE INVENTION

This invention is based on the discovery that certain novel 5-formimidoyl 1,2,3-triazoles as well as substituted derivatives thereof have a surprisingly and unexpectedly high degree of activity against coccidiosis of poultry. Administration of a small amount of at least one of these compounds preferably by combination with poultry feed is effective in preventing or greatly reducing the incidence of coccidiosis. The compounds are effective against both the cecal form (caused principally by *E. tenella*) and the intestinal forms (principally caused by *E. acervulina, E. brunetti, E. maxima* and *E. necatrix*). The coccidiostats of this invention are particularly effective against the species that cause cecal damage in addition to preventing the pathology caused by the coccidia.

The instant compounds are also active against Eimeria spp, in other animals.

It is therefore a primary object of this invention to provide novel 5-((Camino) methylene) amino) 1,2,3-triazoles with appropriate substitutions at the 1, 4 and 5-positions which are useful in the control of coccidiosis. Still another object of this invention is to provide novel feed compositions useful for the prevention and suppression of coccidiosis. A further object of this invention is to provide a new and useful method for the control of coccidiosis in poultry which comprises administering to the poultry minor amounts of the anticoccidial substance of this invention. A still further object of this invention is to provide a method and alternate methods for preparing novel 5-amino and substituted amino 1,2,3-triazoles. These and further objects of this invention will become apparent from reading the following description.

DESCRIPTION OF THE INVENTION

The novel compounds of this invention are best realized in the following structural formula:

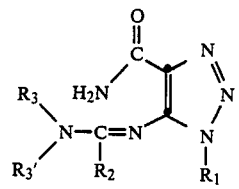

wherein:

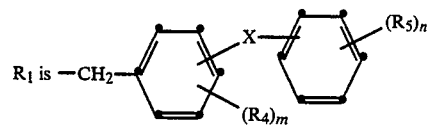

wherein
m is 0 to 4; and n is 0 to 5; X is O, S, SO, $SO_2$, CO, CHCN, $CH_2$ or $C=NR_6$ where $R_6$ is hydrogen, hydroxy, loweralkoxy, or cyano; and, $R_4$ and $R_5$ are independently halogen, cyano, trifluoromethyl, loweralkanoyl, nitro, loweralkyl, loweralkoxy, carboxy, carbalkoxy, trifluoromethoxy, acetamido, or trichlorovinyl; and $R_2$, $R_3$ and $R_3'$ are independently hydrogen or loweralkyl.

The preferred compounds of the instant invention are realized in the foregoing structural formula wherein:

m is 0, 1 or 2 and n is 0 or 1; X is O, S, SO, $SO_2$, $CH_2$, CO or $C=NR_6$ wherein $R_6$ is hydrogen, hydroxy, methoxy or cyano;

$R_4$ is fluoro, chloro, bromo, methyl, trifluoromethyl, cyano, carbomethoxy, trifluoromethoxy, trifluoromethylthio, or trichlorovinyl;

$R_5$ is halogen, methyl, trifluoromethyl, cyano, carbalkoxy, or trichlorovinyl.

The most preferred compounds of the instant invention are realized in the foregoing structural formula wherein m is 1 or 2, n is 1; X is O, $CH_2$ or CO;

$R_4$ is mono- or di-substituted ortho to X and are independently fluoro, chloro, methyl, trifluoromethyl, cyano or carbomethoxy; and $R_5$ is meta or para to X and which is independently fluoro, chloro, methyl, cyano, carbomethoxy or trichlorovinyl.

Examples of compounds of this invention are: 5-(((dimethylamino)methylene)amino)-1-[4-(4-chlorobenzoyl)-3,5-dichlorobenzyl]-1,2,3-triazole-4-carboxamide, 5-(((dimethylamino) methylene)amino)-1-[4-(4-chlorophenylthio)-3,5-dichlorobenzyl]-1,2,3-triazole-4-carboxamide, 5-(((dimethylamino)methylene)amino)-1-[4-(4-chlorophenyl-sulfinyl)-3,5-dichlorobenzyl]-1,2,3-triazole-4-carboxamide, 5-(((dimethylamino)methylene)amino)-1-[4-(4-chlorobenzoyl)-3-chloro -5-methylbenzyl]-1,2,3-triazole-4-carboxamide, 5-(((dimethylamino)methylene)amino)-1-[4-(4-fluorobenzyl)-3,5-dichlorobenzyl]-1,2,3-triazole-4-carboxamide, 5-(((dimethylamino)methylene)amino)-1-[4-(4-iodophenoxy)-3,5-dichlorobenzyl]-1,2,3-triazole-4-carboxamide, 5-(((dimethylamino)methylene)amino)-1-[4-(4-chlorobenzoyl)-3,5-dimethylbenzyl]-1,2,3-triazole-4-carboxamide, 5-(((dimethylamino)methylene)amino)-1-[4-(4-trifluoromethyl-benzoyl) -3-chloro-5-methylbenzyl]-1,2,3-triazole-4-carboxamide, 5-(((dimethylamino)methylene)amino)-1-[4-(4-chlorobenzoyl)-3trifluoromethylbenzyl]-1,2,3-triazole-4-carboxamide, 5-(((dimethylamino)methylene)amino)-1-[4-(3,4-dichlorobenzoyl)-3,5-dichlorobenzyl]-1,2,3-triazole-4-carboxamide, 5-(((dimethylamino)methylene)amino)-1-(4-[1-(3-methylbenzimino)]-3,5-dichlorobenzyl)-1,2,3-triazole-4-carboxamide, 5-(((amino)methylene)amino-1-[4-(4-fluorobenzoyl)-3-chloro-5-methylbenzyl]-1,2,3-triazole-4-carboxamide hydrochloride, 5-(((amino)ethylidine)amino]-1-[4-(4-chlorobenzoyl)-3,5-dichlorobenzyl]-1,2,3-triazole-4-carboxamide hydrochloride, 5-(((amino)ethylidine)amino)-1-[4-(4-fluorobenzyl)-3,5-dichlorobenzyl]-1,2,3-triazole-4-carboxamide hydrochloride, 5-(((amino)ethylidine)amino)-1-[4-(4-iodophenoxy)-3,5n -dichlorobenzyl ]-1,2,3-triazole-4-carb In the instant invention the term "loweralkyl" is intended to include those alkyl groups containing from 1 to 3 carbon atoms. Exemplary of such groups are methyl, ethyl, propyl and isopropyl.

The term "loweralkoxy" is intended to include those alkoxy groups containing from 1 to 3 carbon atoms. Exemplary of such groups are methoxy, ethoxy, propoxy, and isopropoxy.

The term "loweralkanoyl" is intended to include those alkanoyl groups containing 1 to 3 carbon atoms exemplified by formyl, acetyl, and propionyl.

It will be appreciated by those skilled in the art that when $R_3$ or $R_3'$ is hydrogen the compound can exist in a tautomeric form with the double bond shifting from the position shown above to the position between the $R_2$-bearing carbon and the terminal nitrogen atom. The two tautomers are interchangeable and, in fact, both forms may even coexist in the same isolated product. Both such products are intended to be included within the definition of the instant products.

The instant invention is intended to include the salts of the compounds of the above structure. In particular, the acid addition salts of the instant compounds, such as the salts with mineral acids, in particular hydrochloric, nitric, sulfuric acids and the like are considered to be part of the instant invention.

The compounds of the instant invention may be prepared by any one of several processes. The most general process is outlined in the following reaction scheme.

A procedure for preparing the instant compounds is realized in the following reaction scheme:

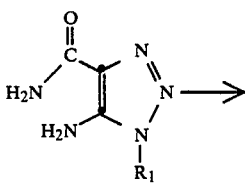

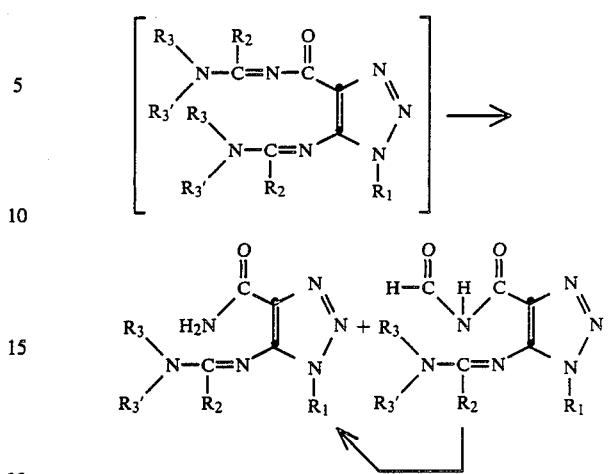

wherein $R_1$, $R_2$, $R_3$ and $R_3'$ are as defined above.

The reaction is carried out in two stages. The first step involves the preparation of the bis amino methylene amino intermediate which is not isolated. The 5-amino starting material is reacted with the appropriately substituted formamide diacetal:

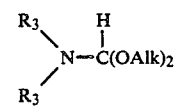

wherein $R_3$ and $R_3'$ are as defined above and Alk is a loweralkyl group. The acetal is used in excess optionally with an inert organic solvent and the reaction is carried out at about room temperature for about 1–5 days. The unstable bis amino methylene amino intermediate spontaneously inverts upon attempted isolation into a 1:1 mixture of the desired product and the formyl derivative thereof. It is not necessary to separate the two compounds and treatment of the mixture with base in a lower alcohol at an elevated temperature up to 70° C. converts the formyl derivatives into the desired product which is isolated using standard techniques.

The reaction scheme for the preparation of those compounds wherein $R_3'$ is hydrogen is as follows:

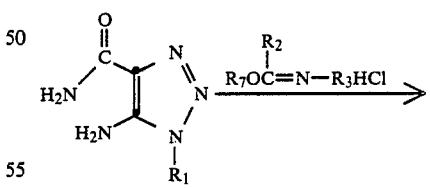

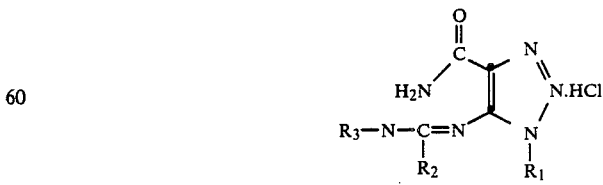

wherein $R_1$, $R_2$ and $R_3$ are as defined above, and $R_7$ is loweralkyl, phenyl or benzyl. The reaction is carried out in a solvent, preferably an alcohol such as methanol or ethanol and is complete in from 1 to 48 hours. The reaction is preferably carried out at the reflux temperature of the reaction mixture, however temperatures of from room temperature to reflux are useful. The products are isolated using known techniques.

The 5-amino starting materials for the foregoing processes are known compounds and are fully described in European patent publication No. 85 300521.3.

The novel compounds of this invention are orally administered to poultry for the control and prevention of coccidiosis. Any number of conventional methods are suitable for administering the coccidiostats of this invention to poultry, as for example, they may be given in the poultry feed. The actual quantity of the coccidiostats administered to the poultry in accordance with this invention will vary over a wide range and be adjusted to individual needs, depending upon species of the coccidia involved and severity of the infection. The limiting criteria are that the minimum amount is sufficient to control coccidiosis and the maximum amount is such that the coccidiostat does not cause any undesirable effects.

A feed typically contains from about 0.0001 to about 0.2 percent, preferably from about 0.001 to about 0.1 percent, by weight of one of the coccidiostats of this invention. The optimum levels will naturally vary with the specific compound utilized and species of Eimeria involved, and can be readily determined by one skilled in the art. Levels of the 5-amino and substituted amino 1,2,3-triazoles of this invention, in poultry feed of from about 0.001 percent to about 0.1 percent by weight of the diet are especially useful in controlling the pathology associated with *E. tenella*, as well as the intestinal dwelling species.

Depending on the compound employed, levels as low as 0.0001 percent possess the novel effects of reducing the number of oocysts passed in the droppings of infected chickens.

The quantity or concentration of a novel coccidiostat of this invention in any admixture in which it is administered to the poultry will, of course, vary in accordance with the type of admixture utilized.

Of the various methods of administering the coccidiostats of this invention to poultry, they are most conveniently administered as a component of a feed composition. The novel coccidiostats may be readily dispersed by mechanically mixing the same in finely ground form with the poultry feedstuff, or with an intermediate formulation (premix) that is subsequently blended with other components to prepare the final poultry feedstuff that is fed to the poultry. Typical components of poultry feedstuffs include molasses, fermentation residues, corn meal, ground and rolled oats, wheat shorts and middlings, alfalfa, clover and meat scraps, together with mineral supplements such as bone meal and calcium carbonate and vitamins.

EXAMPLE 1

5-((dimethylamino)methylene)amino)-1-[4-(4-chlorobenzyl)-3,5dichlorobenzyl]-1,2,3-triazole-4-carboxamide A mixture of 200 mg of 5-amino-1-[4-(4-chlorobenzoyl)-3,5-dichlorobenzyl-1,2,3-triazole-4-carboxamide and 6 ml N,N-dimethylformamide dimethylacetal is stirred at room temperature under a nitrogen atmosphere for 5 days. Most of the N,N-dimethylformamide dimethylacetal is removed under high vacuum at 45° C. and the residue is applied to a 1000 μ silica gel preparative layer chromatography plate (20×20 cm) and eluted with a solvent mixture of 10% methanol in chloroform. Two major bands were observed and eluted with 25% methanol in methylene chloride; a faster moving band (A, 92 mg) and a slower band (B, 150 mg). Thin layer chromatography showed that band B had decomposed into two new products, both of which were the main components of band A. Bands A and B were separately chromatographed on preparative layer chromatography plates with band A being divided among two plates and band B being divided among three plates and the plates being eluted with 10% methanol in chloroform. The faster bands on each plate were removed from the silica gel with 25% methanol in methylene chloride and evaporated in vacuo to give 103 mg of a compound that nuclear magnetic resonance and mass spectrometry indicate to be 5-((dimethylamino)methylene)amino)-1-[4-(4-chlorobenzyl)-3,5-dichlorobenzyl]-1,2,3-triazole-4-N-formylcarboxamide. The slower band was similarly extracted affording 68 mg of 5-((dimethylamino)methylene)amino)-1-[4-chlorobenzyl)-3,5dichlorobenzyl]-1,2,3-triazole-4-carboxamide, the desired product.

The faster moving N-formylcarboxamide compound (10 mg) was hydrolyzed in 14 ml of methanol with 1.3 ml of 2.5M NaOH. The solution is allowed to stand at room temperature for 45 minutes. Thin layer chromatography showed that the N-formylcarboxamide was gone and only product was present. The pH was adjusted to 8 with acetic acid, 7 ml of water was added and the methanol evaporated in vacuo. The crystals are filtered, washed with water, dried and combined with the first batch of product to afford a total of 88 mg of pure product. Mass spectrum: m/e 478, 480 (M+). NMR (DMSO-d6): 9.05 (s, 1H, N=CH—N), 7.76 (q, 4H,

7.61 (s, 2H,

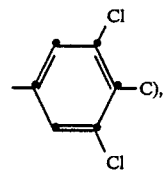

5.56 (s, 6H, N(CH3)2).

EXAMPLE 2

5-((amino)ethylidine)amino)-1-[4-(4-chlorobenzoyl)-3,5-dichlorobenzyl]-1,2,3-triazole-4-carboxamide hydrochloride A mixture of 5-amino-1-[4-(4-chlorobenzoyl)-3,5-dichlorobenzyl]-1,2,3-triazole-4-carboxamide (4.3 g), ethyl acetimidate hydrochloride (1.2 g) and absolute ethanol (50 ml) is heated at reflux under nitrogen for 20 hours. The reaction mixture is cooled and diluted with ethyl ether (50 ml). The solid is filtered and dried to give 5-((amino)ethylidine) amino)-1[4-(4-chlorobenzoyl)-3,5-dichlorobenzyl]-1,2,3-triazole-4-carboxamide hydrochloride.

What is claimed is:

1. A compound having the formula:

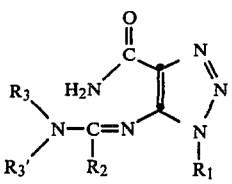

wherein:

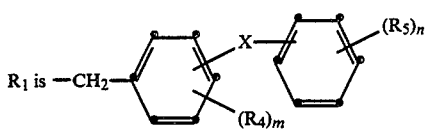

wherein
m is 0 to 4; and n is 0 to 5; X is O, S, SO, $SO_2$, CO, CHCN, $CH_2$ or C=$NR_6$ where $R_6$ is hydrogen, hydroxy, loweralkoxy, or cyano; and, $R_4$ and $R_5$ are independently halogen, cyano, trifluoromethyl, loweralkanoyl, nitro, loweralkyl, loweralkoxy, carboxy, carbalkoxy, trifluoromethoxy, acetamido, or trichlorovinyl;

, $R_2$, $R_3$ and $R_3'$ are independently hydrogen or loweralkyl; and salts thereof.

2. The compound of claim 1 wherein m is 0, 1 or 2, n is 0 or 1; X is O, S, SO, $SO_2$, $CH_2$, CO or C=$NR_6$ wherein $R_6$ is hydrogen, hydroxy, methoxy or cyano;

$R_4$ is fluoro, chloro, bromo, methyl, trifluoromethyl, cyano, carbomethoxy, trifluoromethoxy, trifluoromethylthio, or trichlorovinyl;

$R_5$ is halogen, methyl, trifluoromethyl, cyano, carbalkoxy, or trichlorovinyl.

3. The compound of claim 2 wherein m is 1 or 2, n is 1; X is O, $CH_2$ or CO;

$R_4$ is one or two substituents ortho to X and are independently fluoro, chloro, methyl, trifluoromethyl, cyano or carbomethoxy; and $R_5$ is meta or para to X and which is independently fluoro, chloro, methyl, cyano, carbomethoxy or trichlorovinyl.

4. The compound of claim 1 which is 5-(((dimethylamino)methylene)amino)-1-[4-(4-chlorobenzoyl)-3-trifluoromethylbenzyl]-1,2,3-triazole-4-carboxamide.

5. The compound of claim 1 which is 5-(((dimethylamino)methylene)amino)-1-[4-(4-chlorobenzoyl)-3,5dichlorobenzyl]-1,2,3-triazole-4-carboxamide.

6. The compound of claim 1 which is 5-(((dimethylamino)methylene)amino)-1-[4-(4-chlorophenylthio)3,5-dichlorobenzyl]-1,2,3-triazole-4-carboxamide.

7. The compound of claim 1 which is 5-(((dimethylamino)methylene)amino)-1-[4-(4-chlorophenyl-sulfinyl) -3,5-dichlorobenzyl]-1,2,3-triazole-4-carboxamide.

8. The compound of claim 1 which is 5-(((dimethylamino)methylene)amino)-1-[4-(4-chlorobenzoyl)-3-chloro-5-methylbenzyl]-1,2,3-triazole-4-carboxamide.

9. The compound of claim 1 which is 5-(((dimethylamino)methylene)amino)-1-[4-(4-chlorobenzoyl)-3,5-dimethylbenzyl]-1,2,3-triazole-4-carboxamide.

10. The compound of claim 1 which is 5-(((dimethylamino)methylene)amino)-1-[4-(4-trifluoromethylbenzoyl)-3-chloro-5-methylbenzyl]-1,2,3-triazole-4carboxamide.

11. The compound of claim 1 which is 5-(((dimethylamino)methylene)amino)-1-[4-(3,4-dichlorobenzoyl)-3,5-dichlorobenzyl-1,2,3-triazole-4-carboxamide.

12. The compound of claim 1 which is 5-((amino)methylene)amino)-1-[4-(4-fluorobenzoyl)-3-chloro-5-methylbenzyl]-1,2,3-triazole-4-carboxamide hydrochloride.

13. The compound of claim 1 which is 5-(dimethylamino)methylene)amino)-1-[4-(4-fluorobenzoyl)-3,5-dichlorobenzyl]-1,2,3-triazole-4-carboxamide.

14. The compound of claim 1 which is 5-(dimethylamino)methylene)amino)-1-[4-(4-iodophenoxy)-3,5-dichlorobenzyl]-1,2,3-triazole-4-carboxamide.

15. The compound of claim 1 which is 5-((amino)ethylidine)amino)-1-[4-(4-chlorobenzoyl)-3,5-dichlorobenzyl]-1,2,3-triazole-4-carboxamide.

16. A method for preventing or treating coccidiosis which comprises administering to an animal in need of such treatment an effective amount of a compound of claim 1.

17. A composition useful for the prevention and treatment of coccidiosis which comprises an inert carrier and an effective amount of a compound of claim 1.

* * * * *